United States Patent
Cibulski

(10) Patent No.: US 10,149,959 B1
(45) Date of Patent: Dec. 11, 2018

(54) NIGHT LAMP WITH INTEGRATED WATER FEATURES

(71) Applicant: Anthony A. Cibulski, Birmingham, AL (US)

(72) Inventor: Anthony A. Cibulski, Birmingham, AL (US)

( * ) Notice: Subject to any disclaimer, the term of this patent is extended or adjusted under 35 U.S.C. 154(b) by 0 days.

(21) Appl. No.: 15/715,365

(22) Filed: Sep. 26, 2017

(51) Int. Cl.
| A01K 63/06 | (2006.01) |
| A61M 21/02 | (2006.01) |
| F21V 23/00 | (2015.01) |
| F21S 10/00 | (2006.01) |
| F21Y 105/10 | (2016.01) |
| A61M 21/00 | (2006.01) |
| F21Y 113/13 | (2016.01) |
| F21Y 115/10 | (2016.01) |

(52) U.S. Cl.
CPC .......... *A61M 21/02* (2013.01); *F21S 10/002* (2013.01); *F21V 23/001* (2013.01); *A61M 2021/0027* (2013.01); *A61M 2021/0044* (2013.01); *F21Y 2105/10* (2016.08); *F21Y 2113/13* (2016.08); *F21Y 2115/10* (2016.08)

(58) Field of Classification Search
None
See application file for complete search history.

(56) References Cited

U.S. PATENT DOCUMENTS

| 3,563,204 | A | * | 2/1971 | Szilagyi | ............... | A01K 63/06 119/267 |
| 3,908,598 | A | * | 9/1975 | Jewson | ............... | A01K 63/006 119/267 |
| 4,133,024 | A | * | 1/1979 | Roehrick | ............... | A01K 63/06 119/246 |
| 7,500,776 | B1 | * | 3/2009 | Buczko | ............... | A01K 63/06 119/267 |
| 9,603,346 | B2 | * | 3/2017 | Lutz | ............... | A01K 63/06 |
| 2003/0116489 | A1 | * | 6/2003 | Terato | ............... | A01K 63/045 210/167.21 |
| 2008/0004181 | A1 | * | 1/2008 | Yoshikawa | ............... | A01K 63/04 504/150 |

* cited by examiner

*Primary Examiner* — Elmito Breval
(74) *Attorney, Agent, or Firm* — Shifrin Patent Law; Dan Shifrin

(57) ABSTRACT

A night light with integrated water features is provided. Changing audial frequencies are generated by the cavitation bubbles in the lower chamber and simulate the tranquil, calming effects of gently tumbling waves on a beach. The cavitation bubbles also sparkle with color when illuminated by lighting below the lower chamber, providing substantial augmentation of the visual display. Colorful beads in the bead chamber are propelled in graceful random multidirectional movements, simulating the unpredictable movements of fish. Thus, the night lamp with integrated water features may serve as a maintenance free surrogate fish bowl.

2 Claims, 4 Drawing Sheets

NIGHT LAMP WITH INTEGRATED WATER FEATURES

RELATED APPLICATION DATA

The present application is related to commonly-owned and co-pending U.S. application Ser. No. 15/201,407 entitled ACRYLIC WATER FEATURES, filed on Jul. 2, 2016, which application is incorporated herein by reference in its entirety.

TECHNICAL FIELD

The present invention relates generally to lighting systems and, in particular, to a night lamp with integrated water features.

BACKGROUND ART

In an era of extreme stress and insane chaos, the demand for anxiolytics, anti-depressants and insomniolytics has increased at an alarming rate. Therefore, there have been efforts made in the development of non-pharmaceutical strife liberating approaches to conquer these personal burdens.

Water displays have been developed for providing a serene and relaxing visual and audial effect for the user. Conventional water displays, such as those designed for a desk or table top, are non-dynamic and unchanging, resulting in eventual apathy and disinterest. These conventional water displays often lack illumination and are devoid of any changing water patterns and, therefore, produce the same auditory frequencies.

Similarly, conventional night lights are merely functional in that they only provide a small amount of light but otherwise offer nothing of interest.

SUMMARY OF THE INVENTION

Embodiments of the present invention provide a night light with integrated water features. Changing audial frequencies are generated by the cavitation bubbles in the lower chamber and simulate the tranquil, calming effects of gently tumbling waves on a beach. The cavitation bubbles also sparkle with color when illuminated by lighting below the lower chamber, providing substantial augmentation of the visual display. Colorful beads in the bead chamber are propelled in graceful random multidirectional movements, simulating the unpredictable movements of fish. Thus, the night lamp with integrated water features may serve as a maintenance free surrogate fish bowl.

DETAILED DESCRIPTION OF THE PREFERRED EMBODIMENT

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Figure 1:
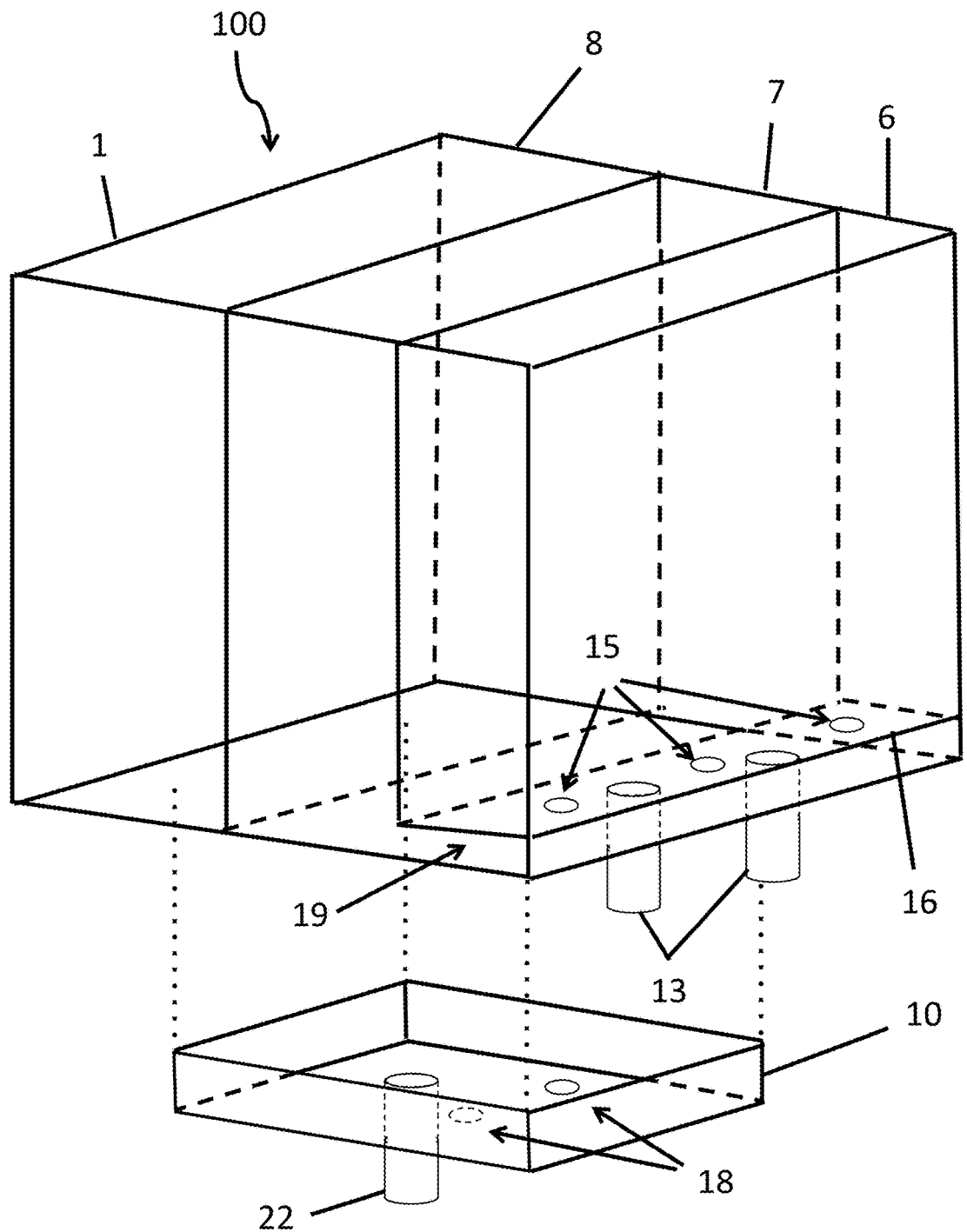
FIG. 1 is a see-through perspective view of the upper chamber of an embodiment of a night lamp of the present invention.
Figure 2:
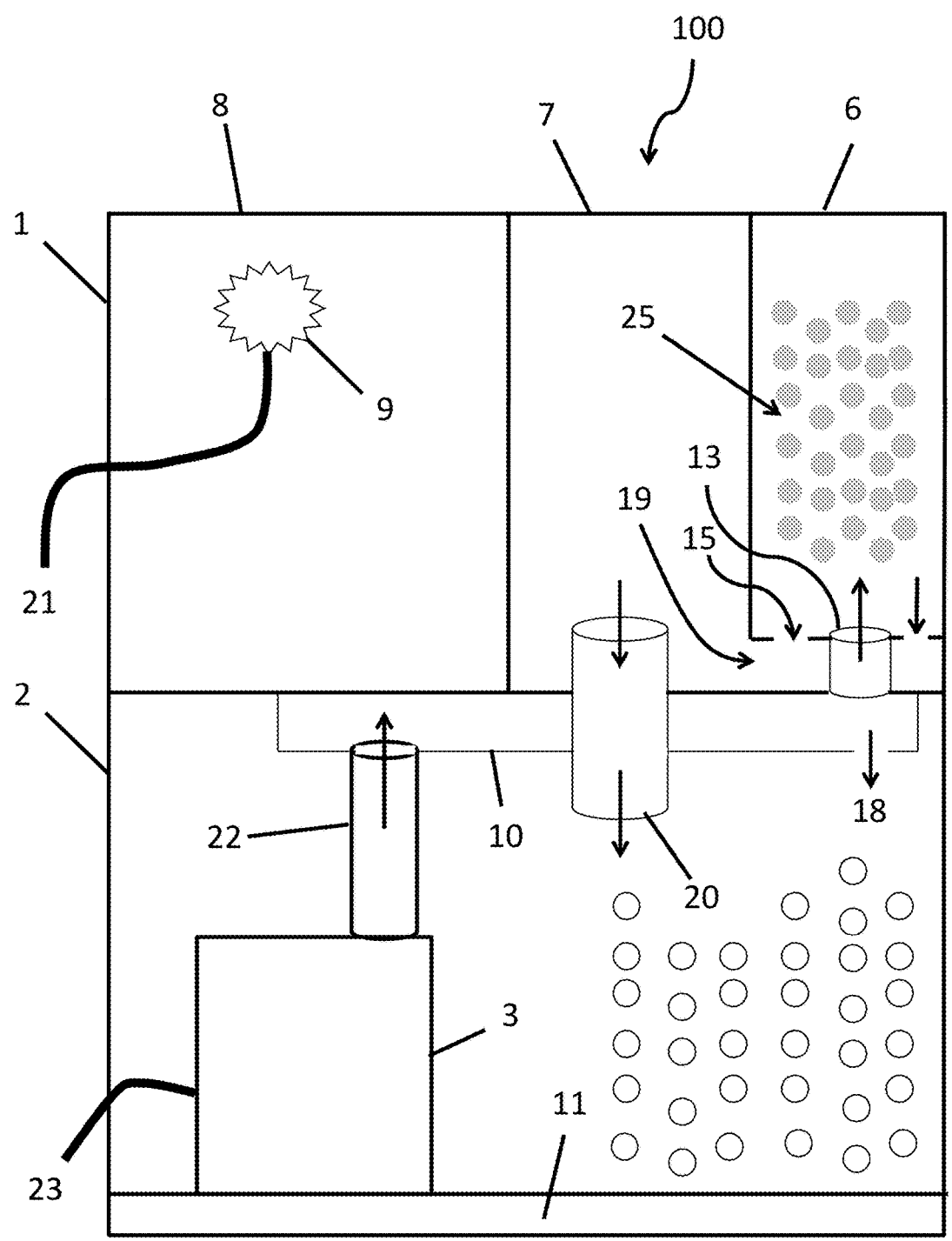
FIG. 2 is a cross-sectional side view of the night lamp of FIG. 1.
Figure 3:
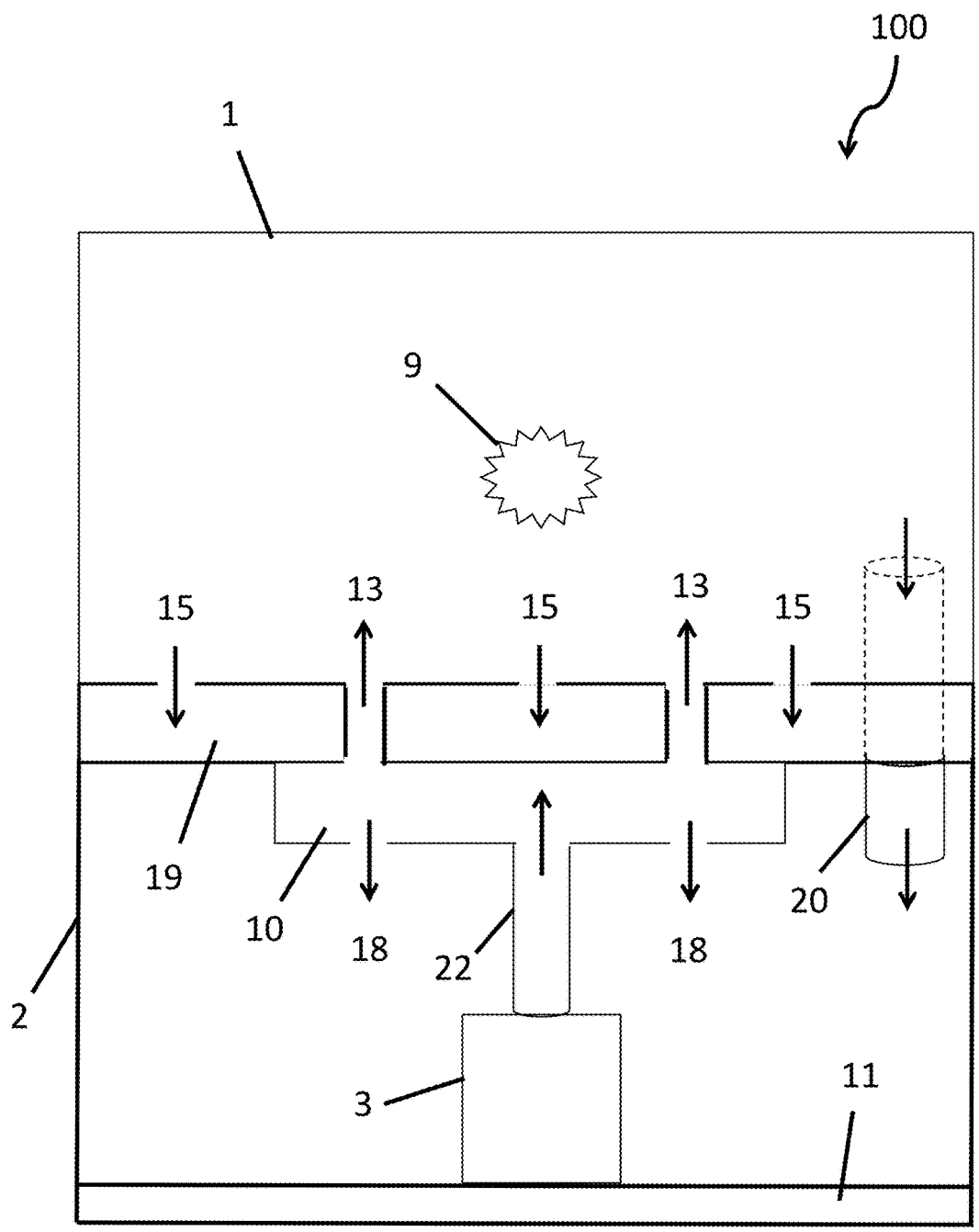
FIG. 3 is a front view of the night lamp of FIG. 1.

FIG. 1 is a see-through perspective view of the upper chamber 1 of an embodiment of a night lamp 100 of the present invention and FIG. 2 is a cross-sectional side view and FIG. 3 is a front view of the night lamp 100. The upper and lower chambers 1, 2 are separated by a pressure chamber 10. The upper chamber 1 is separated into three sub-chambers. From front to back, the upper chamber 1 includes a bead chamber 6, a siphon chamber 7, and a posterior chamber 8. The top edges of all three sub-chambers 6, 7, 8 are the same height such that a cover may be secured over the sub-chambers 6, 7, 8. The bottom 16 of the bead chamber 6 is located a small distance above the top of the pressure chamber 10. The space between the top of the pressure chamber 10 and the bottom of the bead chamber 6 is an atrium 19 that is open to the siphon chamber 7. The bottom of the bead chamber 6 includes ports 15 into the atrium 19 and tubes 13 through the atrium 19 into the pressure chamber 10.

Small beads 25 partially fill the bead chamber 6. A lamp 9, plants, or both may be secured within the posterior chamber 8. A light panel 11, such as a multi-color LED panel, may be secured to the underside of the lower chamber 2.

Figure 4:
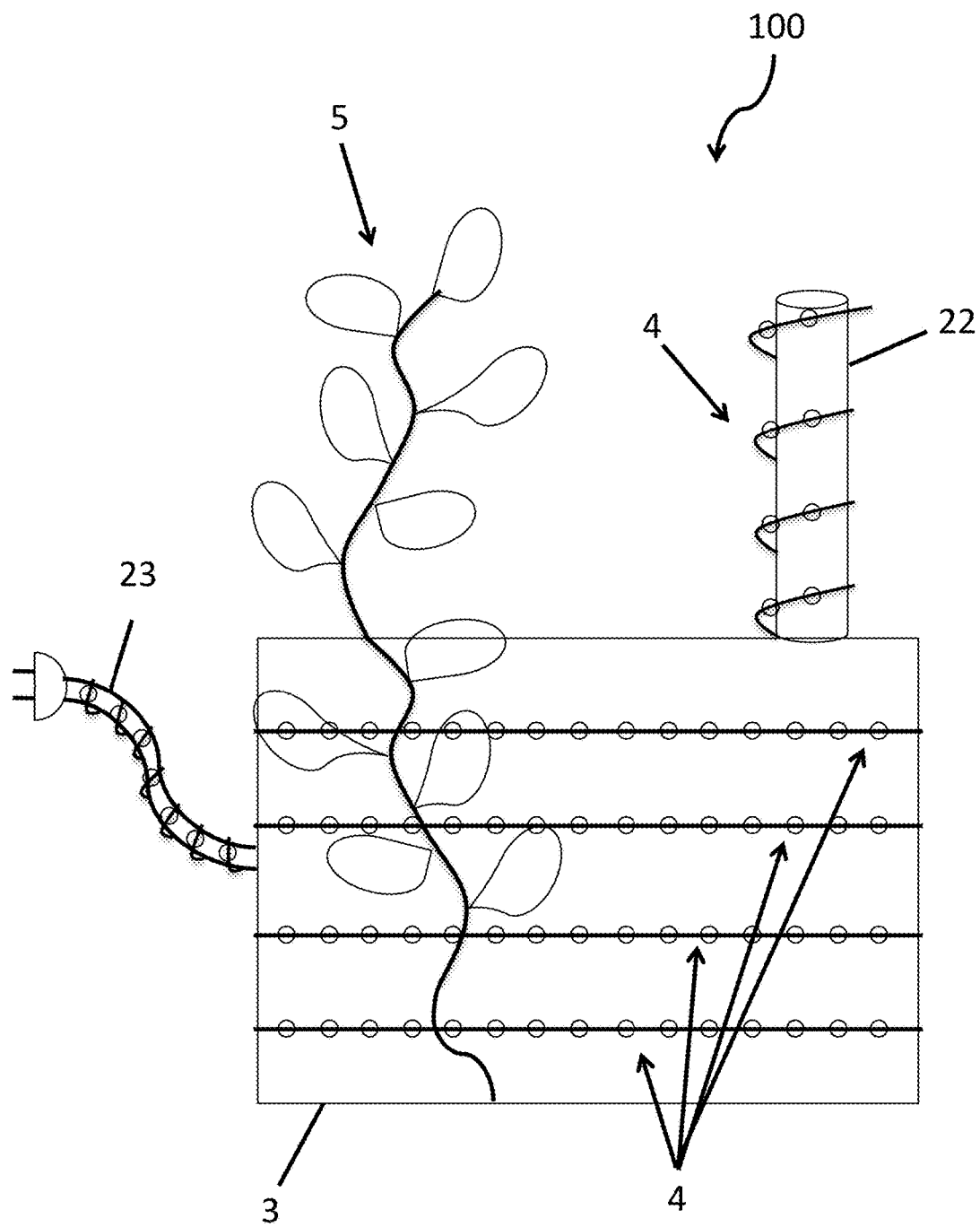
FIG. 4 is a side view of the rear portion of the lower chamber of the night lamp of FIG. 1.

A pump 3 has an inlet to pump water or other fluid from the lower chamber 2 through an outlet tube 22 into the pressure chamber 10. As illustrated in FIG. 4, the pump 3 may be surrounded by beads 4, live or artificial plants 5, or both, or be hidden by any other decorations. The power cord 23 to the pump 3 and the tube 22 may also be wrapped with beads 4. A siphon tube 20 extends from the lower chamber 2, through the bottom of the upper chamber 1, and into the siphon chamber 7.

All side, top, and bottom panels of the upper and lower chambers, 1, 2 and the pressure chamber 10 may be a clear acrylic material allowing one to see into the night lamp 100. In the embodiment illustrated and described, the chambers 1, 2, 10 are box-like in shape having sidewalls and bottoms. The upper and lower chambers 1, 2 have top covers. The dimensions of the night lamp 100 are not critical. One set of dimensions that makes for a convenient, table-top sized display include: the upper chamber 1 is 4"×4"×4"; the lower chamber 2 is 4"×4"×4"; the pressure chamber is 3.5"×2.5"×⅜"; and the atrium 16 is ⅝" high. It will be appreciated that the night light may be constructed using other dimensions and shapes.

When the lower chamber 2 is filled with water and the pump 3 turned on, water is forced through the tube 22 into the pressure chamber 10. From the pressure chamber 10, water is forced through tube 13 into the bead chamber 6. Water also flows downward through the ports 15 in the bottom 16 of the bead chamber 6 into the atrium 19 of the siphon chamber 7. The posterior chamber 8 remains free of water. The intermingling of the upward flows (via tube 13) and the downward flows (via ports 15) in the bead chamber 6 creates multiple vortices and swirls embodied in the water of the bead chamber 6. These vortices and swirls are revealed by the kinetics of the beads 25 which are propelled in graceful random multidirectional vertical and lateral movements. Water also flows between the siphon chamber 7 and the lower chamber 2 through the siphon tube 20 thereby substantially equalizing the water level in the bead chamber 6 and the siphon chamber 7 via ports 15 in the floor of the bead chamber 6. In addition, slowly rising and falling water level in the bead chamber 6 and the siphon chamber 7 replicates rising and failing tides enhancing the movement of beads 25 in the bead chamber 6 particularly when the tide is higher. Openings 18 in the bottom of the pressure chamber 10 produce downward moving jets inside the lower chamber 2, generating discrete columns of cavitation bubbles 17. Reciprocal rising and falling tides also occur in the lower chamber 2, thus the interaction of the downward jets 18 and variable height of water in the lower chamber 2 results in a variation of sounds generated by the bubbles 17 that cycle with the tides of the system. Additionally, the bubbles 17 flow upward into the bead chamber 6 through tubes 13, further augmenting the kinetic display of the beads 25.

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A night light, comprising:
    a pressure chamber having transparent side walls, front wall, top, and bottom;
    a lower chamber having transparent side walls, front wall, and top;
    an upper chamber having transparent side walls, front wall, floor, and top, comprising:
        a posterior chamber against a rear wall of the upper chamber and extending forward, the posterior chamber extending downward from the top to the floor;
        a siphon chamber extending forward from the front of the posterior chamber, the siphon chamber extending downward from the top to the floor;
        a bead chamber extending forward from the front of the siphon chamber to the front wall of the upper chamber, the bead chamber extending downward from the top and having a bottom raised above the floor of the upper chamber;
        an atrium extending downward from the bottom of the bead chamber to the floor, the atrium open to the siphon chamber; and
        a pressure chamber and located at least partially under the posterior, siphon, and bead chambers;
    a water pump having an inlet in the lower chamber;
    a first tube configured to carry fluid pumped from the lower chamber through a discharge outlet of the pump into the pressure chamber;
    a second tube configured to carry fluid from the pressure chamber into the bead chamber;
    the bottom of the bead chamber having a first set of openings, whereby fluid flows from the bead chamber into the atrium;
    a third tube configured to carry fluid from the siphon chamber into the lower chamber;
    the bottom of the pressure chamber having a second set of openings, whereby fluid flows from the pressure chamber into the lower chamber;
    a plurality of beads in the bead chamber; and
    a light in the posterior chamber.

2. The night light of claim 1, further comprising a light panel under the lower chamber.

* * * * *